United States Patent [19]
Harfeldt et al.

[11] Patent Number: 5,646,041
[45] Date of Patent: Jul. 8, 1997

[54] MONOCLONAL ANTIBODY TO HERPES SIMPLEX VIRUS AND CELL LINE PRODUCING SAME

[76] Inventors: Elisabeth Harfeldt, 19 Catalpa Rd., Convent Station, N.J. 07961; Philip Lake, 70 Brooklawn Dr., Parsippany, N.J. 07950; Barbara Nottage, 1-31 Berdan Ave., Fair Lawn, N.J. 07410; Lars G. Ostberg, 19 Catalpa Rd., Convent Station, N.J. 07961

[21] Appl. No.: 305,683

[22] Filed: Sep. 13, 1994

Related U.S. Application Data

[63] Continuation-in-part of Ser. No. 759,279, Sep. 13, 1991, abandoned, which is a continuation of Ser. No. 355,595, May 22, 1989, abandoned, which is a continuation-in-part of Ser. No. 13,763, Feb. 12, 1987, abandoned.

[51] Int. Cl.$^6$ .......................... C07K 16/00; C12N 5/00; C12N 15/00; C12P 21/04
[52] U.S. Cl. ............................ 435/339.1; 530/388.15; 530/388.3; 435/172.2; 435/70.21
[58] Field of Search ........................ 530/388.15, 388.3; 435/240.27, 172.2, 70.21

[56] References Cited

U.S. PATENT DOCUMENTS

| | | |
|---|---|---|
| 4,634,664 | 1/1987 | Oestberg . |
| 4,757,018 | 7/1988 | Brown .................................. 435/240.2 |

OTHER PUBLICATIONS

Su et al. "Protective Antibody Therapy is Associated with Reduced Chemokine Transcripts in Herpes Simplex Type 1 Corneal Infection", 1996, *Journal of Virology*, vol. 70, No. 2, pp. 1277–1281. *Abstract Only.

Co et al., "Humanized Antibodies for Antiviral Therapy", 1991, *Proceedings of the National Academy of Sciences of the United States of America*, vol. 88, No. 7, pp. 2869–2873. *Abstract Only.

Sanna et al., "Directed Selection of Recombinant Human Monoclonal Antibodies to Herpes Simplex Virus Glycoproteins From Phage Display Libraries", 1995, *Proceedings of the National Academy of Sciences of the United States of America*, vol. 92, No. 14, pp. 6439–6443.

Staats et al., "Anti–Glycoprotein D Monoclonal Antibody Protects Against Herpes Simplex Virus Type 1–Induced Diseases in Mice Functionally Depleted of Selected T–Cell Subsets or Asialo GM1+ Cells", *Journal of Virology*, 1991, vol. 65, No. 11, pp. 6008–6014.

Lake et al. Prog. Abstr. Interscience Conf. Antimicrob. Agents Chemother. vol. 32:402 1992.

Rudihoff et al., PNAS USA 79:1979–1983, 1982.

Seigneurin et al. Science 221:173–175, 1983.

Goding, "Monoclonal Antibodies: Principles and Practice", Academic Press, 1983 pp. 118–123.

*Primary Examiner*—Marian C. Knode
*Assistant Examiner*—Jay Williams
*Attorney, Agent, or Firm*—Townsend & Townsend & Crew

[57] ABSTRACT

Human Monoclonal antibodies effective for the diagnosis and treatment of Herpes Simplex Virus 1 and 2 have been prepared from a cell line obtained by fusing a xenogeneic hybridoma designated SPAZ 4 with spleen cells of a patient immune to Herpes Simplex Virus.

14 Claims, 2 Drawing Sheets

```
ATG GCC TGG TCT CCT CTC CTC ACT CTC CTC GCT CAC TGC ACA GGG TCC TGG GCC CAG      60
 M   A   W   S   P   L   L   T   L   L   A   H   C   T   G   S   W   A   Q
                                                                         =

TCT GTG CTG ACG CAG CCG CCC TCA GTG TCT GGG GCC CCA GGG CAG GGG GTC ACC CTC TCC 120
 S   V   L   T   Q   P   P   S   V   S   G   A   P   G   Q   G   V   T   L   S

TGC ACT GGG AGC CGC TCC AAC ATC GGG GCA GGT TAT GAT GTA CAC TGG TAC CAG CAC CTT 180
 C   T   G   S   R   S   N   I   G   A   G   Y   D   V   H   W   Y   Q   H   L
 ‗           ‗                       ‗           ‗

CCA GGA ACA GCC CCC AAA CTC CTC ATC TAT GGT GAC AAC AAT CGG CCC TCA GGC ATC CCT 240
 P   G   T   A   P   K   L   L   I   Y   G   D   N   N   R   P   S   G   I   P
                                         ‗           ‗           ‗

GAC CGA TTC TCT GGC TCC AAG TCT GGC ACC TCA GCC TCC CTG GCC ATC ACT GGG CTC CAG 300
 D   R   F   S   G   S   K   S   G   T   S   A   S   L   A   I   T   G   L   Q

GCT GAA GAT GAG GCT GAT TAT TAC TGC CAG TCG TAT GAC AGC AGC GGC CTG AGT GGG TCG ATA 360
 A   E   D   E   A   D   Y   Y   C   Q   S   Y   D   S   S   G   L   S   G   S   I
                                     ‗           ‗                           ‗

TTC GGC GGA GGG ACC AAG CTG ACC GTC CTA GGT                                      390
 F   G   G   G   T   K   L   T   V   L   G
```

FIG. 1A

```
ATG GAG TTT GGG CTG AGC TGG GTT TTC CTC GTT GCT CTT TTA AGA GGT GTC CAG TGT CAG      60
 M   E   F   G   L   S   W   V   F   L   V   A   L   L   R   G   V   Q   C   Q

GTG CAG CTG GTG GAG TCG GGG GGA GGC TTG GTC CAG CCT GGG AGG TCC CTG AGA CTC TCC     120
 V   Q   L   V   E   S   G   G   G   L   V   Q   P   G   R   S   L   R   L   S
                                                                            30

TGT GCA GCG TCT GGA TTC ACC TTC AGT AGC CAT GTC ATG CAT TGG GTC CGC CAG GCT CCA     180
 C   A   A   S   G   F   T   F   S   S   H   V   M   H   W   V   R   Q   A   P
                                                     __  __  __
                                                     150

GGC AAG GGG CTG CAG TGG CTG GCA GTT ATC ATT TCC AGA GAC AAT AGT AAA AAT ATC CTG     240
 G   K   G   L   Q   W   L   A   V   I   I   S   R   D   N   S   K   N   I   L
     __  __  __  __                  __  __  __  __  __  __  __  __  __  __  __
                                     210

GAG TCC GTG AAG GGC CGA TTC ATC ATC TCC AGA GAC AAT TCC AAG AAT ATC CTG TAT CTG     300
 K   E   S   V   G   R   F   I   I   S   R   D   N   S   K   N   I   L   Y   L
 __  __  __  __  __
                                                                            300

CAA ATG AAC AGC CTG AGA GCC GAG GAC ACG GCT GTG TAT TAC TGT GCG AGA GGG GGC TAC     360
 Q   M   N   S   L   R   A   E   D   T   A   V   Y   Y   C   A   R   G   G   Y
                                                                             __

GGA AGG GGG CAC TAC TTC TAC GGT CTG GAC GTC TGG GGC CGA GGG ACC ACG GTC ACC GTC     420
 G   R   G   H   Y   F   Y   G   L   D   V   W   G   R   G   T   T   V   T   V
 __  __  __  __  __  __  __  __  __  __  __

TTC TCA
 F   S
```

FIG. 1B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 426 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..426
( D ) OTHER INFORMATION: /product="HSV863 heavy chain variable region"

( x i ) SEQUENCE DESCRIPTION: SEQ ID NO:1:

```
ATG GAG TTT GGG CTG AGC TGG GTT TTC CTC GTT GCT CTT TTA AGA GGT        48
Met Glu Phe Gly Leu Ser Trp Val Phe Leu Val Ala Leu Leu Arg Gly
 1               5                  10                  15

GTC CAG TGT CAG GTG CAG CTG GTG GAG TCG GGG GGA GGC GTG GTC CAG        96
Val Gln Cys Gln Val Gln Leu Val Glu Ser Gly Gly Gly Val Val Gln
            20                  25                  30

CCT GGG AGG TCC CTG AGA CTC TCC TGT GCA GCG TCT GGA TTC ACC TTC       144
Pro Gly Arg Ser Leu Arg Leu Ser Cys Ala Ala Ser Gly Phe Thr Phe
        35                  40                  45

AGT AGC CAT GTC ATG CAT TGG GTC CGC CAG GCT CCA GGC AAG GGG CTG       192
Ser Ser His Val Met His Trp Val Arg Gln Ala Pro Gly Lys Gly Leu
    50                  55                  60

CAG TGG CTG GCA GTT ACA TGG TAC GAT GGA AGT AAC AAA GCC TAT GGA       240
Gln Trp Leu Ala Val Thr Trp Tyr Asp Gly Ser Asn Lys Ala Tyr Gly
65                  70                  75                  80

GAG TCC GTG AAG GGC CGA TTC ATC ATC TCC AGA GAC AAT TCC AAG AAT       288
Glu Ser Val Lys Gly Arg Phe Ile Ile Ser Arg Asp Asn Ser Lys Asn
                85                  90                  95

ATC CTG TAT CTG CAA ATG AAC AGC CTG AGA GCC GAG GAC ACG GCT GTG       336
Ile Leu Tyr Leu Gln Met Asn Ser Leu Arg Ala Glu Asp Thr Ala Val
            100                 105                 110

TAT TAC TGT GCG AGA GCG GGC TAC GGA AGG GGG CAC TAC TTC TAC GGT       384
Tyr Tyr Cys Ala Arg Ala Gly Tyr Gly Arg Gly His Tyr Phe Tyr Gly
        115                 120                 125

CTG GAC GTC TGG GGC CGA GGG ACC ACG GTC ACC GTC TTC TCA               426
Leu Asp Val Trp Gly Arg Gly Thr Thr Val Thr Val Phe Ser
    130                 135                 140
```

( 2 ) INFORMATION FOR SEQ ID NO:2:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Phe Gly Leu Ser Trp Val Phe Leu Val Ala Leu Leu Arg Gly
 1               5                  10                  15
Val Gln Cys Gln Val Gln Leu Val Glu Ser Gly Gly Gly Val Val Gln
            20                  25                  30
Pro Gly Arg Ser Leu Arg Leu Ser Cys Ala Ala Ser Gly Phe Thr Phe
            35                  40                  45
Ser Ser His Val Met His Trp Val Arg Gln Ala Pro Gly Lys Gly Leu
        50                  55                  60
Gln Trp Leu Ala Val Thr Trp Tyr Asp Gly Ser Asn Lys Ala Tyr Gly
 65                  70                  75                  80
Glu Ser Val Lys Gly Arg Phe Ile Ile Ser Arg Asp Asn Ser Lys Asn
                85                  90                  95
Ile Leu Tyr Leu Gln Met Asn Ser Leu Arg Ala Glu Asp Thr Ala Val
            100                 105                 110
Tyr Tyr Cys Ala Arg Gly Gly Tyr Gly Arg Gly His Tyr Phe Tyr Gly
            115                 120                 125
Leu Asp Val Trp Gly Arg Gly Thr Thr Val Thr Val Phe Ser
        130                 135                 140
```

( 2 ) INFORMATION FOR SEQ ID NO:3:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..393
        ( D ) OTHER INFORMATION: /product="HSV863 light chain
            variable region"

( x i ) SEQUENCE DESCRIPTION: SEQ ID NO:3:

```
ATG GCC TGG TCT CCT CTC CTC CTC ACT CTC CTC GCT CAC TGC ACA GGG    48
Met Ala Trp Ser Pro Leu Leu Leu Thr Leu Leu Ala His Cys Thr Gly
 1               5                  10                  15

TCC TGG GCC CAG TCT GTG CTG ACG CAG CCG CCC TCA GTG TCT GGG GCC    96
Ser Trp Ala Gln Ser Val Leu Thr Gln Pro Pro Ser Val Ser Gly Ala
            20                  25                  30

CCA GGG CAG GGG GTC ACC CTC TCC TGC ACT GGG AGC CGC TCC AAC ATC   144
Pro Gly Gln Gly Val Thr Leu Ser Cys Thr Gly Ser Arg Ser Asn Ile
            35                  40                  45

GGG GCA GGT TAT GAT GTA CAC TGG TAC CAG CAC CTT CCA GGA ACA GCC   192
Gly Ala Gly Tyr Asp Val His Trp Tyr Gln His Leu Pro Gly Thr Ala
        50                  55                  60

CCC AAA CTC CTC ATC TAT GGT GAC AAC AAT CGG CCC TCA GGG GTC CCT   240
Pro Lys Leu Leu Ile Tyr Gly Asp Asn Asn Arg Pro Ser Gly Val Pro
 65                  70                  75                  80

GAC CGA TTC TCT GGC TCC AAG TCT GGC ACC TCA GCC TCC CTG GCC ATC   288
```

-continued

```
Asp Arg Phe Ser Gly Ser Lys Ser Gly Thr Ser Ala Ser Leu Ala Ile
                85                  90                  95

ACT GGG CTC CAG GCT GAA GAT GAG GCT GAT TAT TAC TGC CAG TCG TAT    336
Thr Gly Leu Gln Ala Glu Asp Glu Ala Asp Tyr Tyr Cys Gln Ser Tyr
        100                 105                 110

GAC AGC GGC CTG AGT GGG TCG ATA TTC GGC GGA GGG ACC AAG CTG ACC    384
Asp Ser Gly Leu Ser Gly Ser Ile Phe Gly Gly Gly Thr Lys Leu Thr
        115                 120                 125

GTC CTA GGT                                                         393
Val Leu Gly
    130
```

( 2 ) INFORMATION FOR SEQ ID NO:4:

( i ) SEQUENCE CHARACTERISTICS:
    ( A ) LENGTH: 131 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met Ala Trp Ser Pro Leu Leu Leu Thr Leu Leu Ala His Cys Thr Gly
 1               5                  10                  15

Ser Trp Ala Gln Ser Val Leu Thr Gln Pro Pro Ser Val Ser Gly Ala
            20                  25                  30

Pro Gly Gln Gly Val Thr Leu Ser Cys Thr Gly Ser Arg Ser Asn Ile
        35                  40                  45

Gly Ala Gly Tyr Asp Val His Trp Tyr Gln His Leu Pro Gly Thr Ala
    50                  55                  60

Pro Lys Leu Leu Ile Tyr Gly Asp Asn Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala Asp Tyr Tyr Cys Gln Ser Tyr
        100                 105                 110

Asp Ser Gly Leu Ser Gly Ser Ile Phe Gly Gly Gly Thr Lys Leu Thr
        115                 120                 125

Val Leu Gly
    130
```

MONOCLONAL ANTIBODY TO HERPES SIMPLEX VIRUS AND CELL LINE PRODUCING SAME

CROSS-REFERENCE TO RELATED APPLICATIONS

This is a 37 CFR §1.67 continuation-in-part of U.S. Ser. No. 07/759,279 abandoned filed Sep. 13, 1991, which is a continuation of U.S. Ser. No. 07/355,595, filed May 22, 1989 now abandoned, which is a continuation in part of U.S. Ser. No. 07/013,763, filed Feb. 12, 1987 (now abandoned), each of which is hereby incorporated by reference in its entirety for all purposes.

This invention relates to monoclonal antibodies specific for the herpes simplex virus, to cell lines which produce these antibodies, and to methods of producing the cell lines.

BACKGROUND OF THE INVENTION

The two herpes simplex viruses, HSV-1 and HSV-2 are common human pathogens which generally produce mild and self-limiting diseases such as pharyngitis and recurrent oral lesions e.g. "cold sores". However, under certain circumstances HSV viruses may also produce more serious and even life-threatening infections. The most frequent of these serious diseases are: (1) ocular infections, which may lead to blindness; and (2) serious/potentially fatal infections in immunocompromised individuals such as AIDS patients, cancer patients, transplant recipients, and some newborn infants.

Numerous glycoproteins which are antigenic have been identified on the virion envelope and include those designated gA/B, gC, gD, gE, gG and gH. At least one, gD, appears common to both HSV-1 and HSV-2. Monoclonal antibodies, many of them murine, have been made which are specific to various of these glycoproteins. See, for example, Balachandran, et al., 1982, *Infection and Immunity* vol. 37 (3): 1132–1137; Rector, et al., 1982, *Infection and Immunity* vol. 38 (1): 168–174; and Dix, et al., 1981, *Infection and Immunity* vol. 34 (1): 192–199.

There are a few reports in the literature of human antibodies against HSV. For instance, Erlich, et al., 1986, *Review of Infections Diseases* vol. 8 (Supp. 4): S439–S445 discusses human immunoglobulin G which shows activity against HSV. Seigneurin, et al., 1983, *Science* vol. 221: 173–175 discloses a human monoclonal antibody which binds to glycoprotein gD, and can neutralize, albeit at varying potencies both HSV-1 and HSV-2. This cell line was obtained from Epstein-Barr virus infected bone marrow.

BRIEF DESCRIPTION OF FIGURES

FIG. 1. Sequences of the 64-863 antibody light chain (A) and heavy chain (B) variable region cDNAs (SEQ. ID. Nos. 3 and 1) and the translated amino acid sequences (1-letter code) (SEQ. ID. Nos. 4 and 2). The first amino acid of the mature light chain and of the mature heavy chain is double underlined, and the three complementarity determining regions (CDRs) in each chain are underlined.

DETAILED DESCRIPTION OF THE INVENTION

This invention provides for human monoclonal antibodies which are able to bind to the glycoproteins gD antigen of HSV-1 and HSV-2 and are able to neutralize HSV-1 and HSV-2 with substantially equivalent potency. This invention also provides for a virus-free cell line which produces human monoclonal antibodies which are able to bind to the glycoprotein D antigen of HSV-1 and HSV-2. In one embodiment of this aspect of the invention, the cell line is a xenogeneic hybridoma, i.e., a cell which results from the fusion of cells from different species.

A further aspect of this invention is a cell supernatant which comprises a human monoclonal antibody (Mab) able to bind to the glycoprotein gD antigen of HSV-1 and HSV-2 and is also able to neutralize HSV-1 and HSV-2 with substantially equivalent potency, the supernatant being substantially free from any other antibody.

Another aspect of this invention is use of the aforementioned antibodies in vivo to prevent or lessen the severity of HSV-1 and/or HSV-2 infections. Thus a further aspect of this invention is a method of preventing or lessening the severity of HSV-1 or HSV-2 symptoms by administering to a mammal in need of such treatment a symptom-lessening or symptom-preventing amount of a human monoclonal antibody which is able to bind to the glycoprotein gD antigen and neutralize the virus.

The hybridomas of this invention can be made by fusing an immortalized cell to another cell which is chosen for its ability to produce antibodies to the desired antigen. See, e.g. Kohler and Milstein, 1975 *Nature* v 256 495–497. However there have been problems in developing hybridomas which stabily produce human monoclonal antibodies using the Kohler-Milstein technique. It was discovered by Ostberg that xenogeneic triomas, made by using a xenogeneic hybridoma fusion partner which has lost its ability to produce immunoglobins as the immortalizing cell, are more stable and produce antibodies efficiently. This procedure is described in detail in U.S. Pat. No. 4,634,664 and in *Hybridoma* 1983 vol. 2(4): 361 which are hereby incorporated by reference.

In a preferred embodiment of this invention, the hybridoma is a xenogeneic trioma which produces human monoclonal antibodies against the glycoprotein gD antigen of HSV-1 and HSV-2. More particularly, it has now been found that cell lines comprising a parent rodent immortalizing cell, such as a murine myeloma cell, e.g. SP-2, when fused to a human partner cell results in immortalizing xenogeneic hybridoma cells, which, when fused to cells capable of producing an antibody against Herpes Simplex Virus I and II (HSV I and II), provide a novel cell lines capable of generating human antibody effective against such virus in the human.

The publications earlier referred to describe the preparation of a xenogeneic hybridoma referred to as SPAZ 4, prepared from cell line SP-2 obtainable, e.g., from the NIGMS Human Genetic Mutant Cell Repository Ref. CM35669A (see U.S. DHHS 1982 Catalog of Cell Lines). This SP-2 cell line is drug resistant and is fused with normal human peripheral lymphocytes by conventional techniques. A large number of hybrids is obtained and, after approximately five weeks, five clones are selected which show fast growth and no antibody production. These cells are selected for resistance to 8-azaguanine and with three of these lines it is possible to obtain mutants which are resistant to 20 g/mL of 8-azaguanine. These cells are at the same time sensitive to Hypoxanthine-Aminopterin-Thymidine (HAT) medium which showed that they had lost their ability to produce hypoxanthine phosphoribosyl transferase. One of these cell lines is SPAZ 4.

Two methodologies were used to make the monoclonal antibodies of this invention. Both use the cell line SPAZ 4. Cell line SPAZ 4 may be fused with spleen cells obtained from an individual whose spleen is sensitized with HSV I or HSV II antigen. It was found in the first methodology that both hybridoma-like cells and lymphoblastoid cells (spontaneously Epstein-Barr Virus (EBV) transformed) were obtained after such fusion. Contrary to what was hoped, cloning of the hybridoma-like cells failed to generate the fused cells desired. Instead, after great difficulty, a lymphoblastoid cell is re-fused to SPAZ 4 and resulting cell line having hybridoma-like morphology, designated SB IV-6-2 produces antibodies which neutralize HSV I and HSV II in vitro, in some cases at concentrations as low as 50 ng/mL.

It has been found that SB IV-6-2 when tested in mice injected with HSV II is effective in protecting such mice at a dosage of 100 µg/animal (4 mmg/kg).

The second methodology involved fusion of SPAZ 4 cells with spleen cells responding in vitro to heat inactivated HSV-1 antigens. One cell line obtained in this way is designated 64-863. The 64-863 cell line is extremely stable over time; it has been in culture over 12 months. One of the surprising traits of this cell line is that it can produce a high yield of antibody. This is particularly advantageous for scale up production of commercial quantities of antibody.

The preferred monoclonal antibody of this invention is produced by cell line 64-863 and is also designated 64-863. It has been suprisingly found that the potency of 64-863 substantially exceeds that of any other known anti-HSV preparation.

Monoclonal antibody 64-863 belongs to the IgG1 class. It has lambda light chains. It was also found to bind to *Staphylococcus aureus* protein A (SpA). This property is particularly advantageous because binding to SpA provides an efficient, specific and economical method to purify antibodies using a single step technique.

Mab 64-863 was shown to be specific for HSV viruses. It reacted with 15 independent isolates of HSV-1 and HSV-2, but no cross reactivity was observed with uninfected VERO cells or with varicella-zoster virus. Further and suprisingly, 64-863 was found to neutralize both HSV-1 and HSV-2 substantially equally, and with a surprising potency. It is believed that 64-863 is the most potent HSV neutralizing monoclonal antibody of any origin to date.

The monoclonal antibodies of this invention are particularly well suited for clinical and diagnostic use but especially for clinical use.

The preferred monoclonal antibody of this invention, 64-863, has been shown to protect mice from both HSV-1 and HSV-2 infection. The antibodies may be administred prior to infection or even after infection. For HSV-1, the antibody was strongly protective up to 24 hours after infection and was protective, albeit to a lesser degree, for 48 hours thereafter.

For HSV-2 infections, the antibody was strongly protective even at 48 hours post-infection. Antibody 64-863 was also shown to be effective in lessening the symptoms of HSV cutaneous disease, when administered after infection. This is an especially surprising result given the short half-life of human monoclonal antibodies in mice.

Thus, an important aspect of this invention is the use of the antibodies of the present invention for both their prophylactic and therapeutic benefits in mammals, and especially in humans. The HSV diseases particularly targeted include primary or reactivation disease in immunocompromised patients (e.g. bone marrow and other transplated patients, cancer therapy patients, and AIDS patients). For these patients, the probablity of iatrogenic HSV disease often exceeds 50% and the HSV infection can be severe and even life-threatening.

Presently Acyclovir (9-[(2-hydroxyethetyl)-methyl] guanine), may be used as prophylaxis in some circumstances, but not in all cases. Published data suggests that transplacentally-derived antibody affects the outcome of infection after human neonatal exposure to HSV. The antibody appears to completely neutralize virus in some infants and prolongs the incubation period and modifies the infection in others (Yeager A. S. et al *Infection and Immunity*, 29:532–538, 1980, Sullender W. M. et al *J. Inf. Dis.* 155: 28–37, 1987). An estimate of the dose of commercial immune globulin which would be required to achieve prophylaxis of newborn infants at risk concluded that at least 100 ml (approximately 5 g) of immune globin would be needed. This high dose of conventional immune globulin containing only in part, functionally active anti-HSV antibodies, is difficult or impossible to administer, and side-effects may be severe. However, a preparation of monoclonal antibody, in which all molecules are functionally active could achieve efficacy at much lower and more manageable doses. This improved efficacy may be seen in neonates in which prophylactic antibody results in complete absence of disease or in greatly reduced severity or modified duration of incubation of disease and reduced latent infection. Improved efficacy may also be observed in neonates, children or adults in which monoclonal antibody administered therapeutically (i.e. after virus infection is evident) reduces latent virus infection and lessens the severity of HSV disease.

The benefits include but are not limited to decreasing latent vital infection and symptoms and sequelae of HSV disease; extending the incubation time of infection which would create an extended time for clinicians to a definitively diagnose the HSV infection; and providing a more slowly envolving illness from which the efficacies other therapies (e.g. acyclovir) would benefit. Using the monoclonal antibodies of the present invention, either as a replacement for, or administered along with Acyclovir, would be especially valuable for patients with impaired renal function, those with ocular or CNS disease, and those having or at risk to develop Acyclovir-resistant variants. (Recently there have been reports of Acyclovir-resistant virus strains. See, e.g. Schinazi et al 1986. *J. Antimicrobial Chemotherapy* 18 (Supp B):127–134; Chatis et al, 1989. *New Eng J. Med* 320(5): 297–300; and Erlich et al 1989. *New Eng J. Med* 320(5): 293–296).

From animal studies, it can be concluded that the antibodies of this invention are safe even at high doses and can provide prophylactic cover with a half-life of 2–3 weeks. An additional result of monoclonal antibody therapy is the reduction of colonization and latency by HSV primary infections; this is especially relevant to pediatric patients.

The antibodies of the present invention are particularly useful in providing pre-or postexposure prophylactic cover to neonates at risk in acquiring HSV disease since morbidity and sequelae are severe in this patient group despite currently available therapies. Animal studies have shown that neonates can be protected even when antibody administration is delayed 24 hours or more after infection. Since HSV disease evolves more slowly in man, including infants, the opportunity to administer beneficial antibody may extend for a considerably longer time. Administration of the antibody decreases the attack rate (proportion of patients who become infected relative to those at risk) and reduces the severity and rate of progession and dissemination of disease. This could provide critical time to establish a definitive diagnosis of HSV (by virus culture) and to initiate Acyclovir and additional monoclonal antibody therapy as well as to provide additional time for infant immunological maturation. It is particularly in the immediate perinatal period (0 to 6 weeks) in which infants are especially vulnerable to the devastating form of HSV disease.

The antibodies of this invention are also useful in the treatment of ocular HSV infections (250,000–500,000 per year in the U.S.A.). Again, in primary disease, the antibodies can ameliorate symptoms (in possible synergy with Acyclovir) and interfere with establishment of latency. This would offer great value since a large proportion of patients later reactivate latent ocular HSV infections and some progress to blindness.

The antibodies of this invention are thus suitable for parenteral therapy for prophylaxis of HSV in a variety of patients and for many clinical presentations of HSV disease. They are especially suited in instances of low index of suspicion, where drug therapy may be contraindicated or undesirable, since they have no mechanistic toxicity and do not possess any inherent toxicity or side effects.

Antibody 64-863 is the most potent neutralizing antibody yet to be reported and shows an extremely broad reactivity with all HSV-1 and HSV-2 isolates. As an IgG1 antibody, it can mediate immunological effects via several potential mechanisms: steric interference upon binding to virus, complement activation through classical or alternate routes, inhibition of cell to cell spread of virus, opsonization mediated by Fc receptors on mononuclear and polymorphonuclear phagocytes and antibody-dependent cellular cytotoxicity (ADCC). Mab 64-863 can thus independently or in collaboration with serum complement and cellular elements, direct immune effector responses to free virions or to vital antigens expressed on newly infected cells. These multiple mechanisms likely account for the high in vivo biological activity of 64-863, and 64-863 will be highly effective as a sole treatment.

Another aspect of this invention is the antibody fragments, e.g. Fabs which retain the ability to bind to the HSV antigen.

The invention is better illustrated by reference to the following, non-limiting examples.

EXAMPLE 1

Production of Cell Line SB-IV-6-2

Spleen cells from spleen donor SB IV are sensitized with a dilution of soluble HSV II-antigen. Aproximately $3 \times 10^8$ cells are cultivated in 150 milliliters of RPMI-1640 and 5% human serum. After 7 days of culture $3 \times 10^7$ viable cells are recovered and fused to a similar number of SPAZ-4 cells (passage 58). When the supernatants of the cultures are tested (after three weeks), some cultures are positive in an ELISA test to detect anti-HSV antibodies. One of these cultures is designated SB IV-6-2, and it is consistently positive in ELISA tests both on HSV II as well as on HSV I. It also shows neutralizing capacity against HSV II virus. The culture, however, contains both hybridoma-like cells and lymphoblastoid cells and the supernatant contains antibodies of both the IgG and IgM class. The antibodies also have light chains of both kappa and lambda types. After performing some unsuccessful experiments to clone the positive cells, it was subjectively estimated that the larger the proportion of lymphoblastoid cells in the culture the higher the antibody concentration. Addition of oubain exterminated the lymphoblastoid cells and the antibody disappeared. The lymphoblastoid cells were grown in a larger scale and approximately 6 months after the original fusion, the lymphoblastoid cells were fused to the SPAZ-4 cell line (passage 116). The selection procedure is the standard HAT-treatment but with an addition of $2 \times 10^{-7}$M oubain to suppress the growth of unfused lymphoblastoid cells. This fusion yielded several cultures with antibodies against HSV and with cells of hybridoma-like morphology. The best growing of these cell lines, which is still designated SB IV-6-2 (deposited with American Type Culture Collection, 12301 Parklawn Drive, Rockville, Md. 20852, U.S.A. on Feb. 3, 1987 and designated HB 9316), has been cloned and expanded and been found to produce an IgG, kappa-light chain antibody, that binds to the antigens of both HSV I and HSV II and neutralizes both viruses in vitro. The neutralizing capacity is found to be substantially stronger against HSV II and can be detected down to concentrations of 50 ng/mL.

EXAMPLE 2

Use of SB IV-6-2 Antibody In Vivo

An in vivo protection study is performed by pre-treating three-week old Balb/c mice with antibody from SB IV-6-2 and control cells 24 hours prior to footpad injection of 10 LD50-doses of HSV II virus. Two control groups are used, one receiving only saline and one receiving an unrelated human anti-cytomegalovirus antibody. There are 12 animals in each group; in the saline treated group all animals succumbed by day 21. In the group receiving control antibody, one animal is still alive at day 26 and in the antibody treated group five animals are still alive at day 26. The dose of antibody given is 100 mcg per animal. This experimental model involves an infection in the central nervous system since the virus has a capacity of retrograde transport inside nerves. The result is statistically significant if the treated group is compared to the saline group and if the treated group is compared to the combined saline and non-related antibody groups.

EXAMPLE 3

Production of Cell Line 64-863

A. Production of antibody-producing cells

VERO cells are infected with HSV-1 (McIntyre) at an m.o.i.=1 for 48–72 hours. The antigenic cells are harvested, washed in phosphate buffered saline (PBS), diluted in PBS 180 cm$^2$ flask per 10 ml) then sonicated, heat-inactivated 56° C., 30 min.), and then frozen at −80° C. until used.

B. Fusion

After 7 days of culture, in the presence of antigen in RPMI-1640 medium containing 10% human plasma, SBIII human spleen cells are fused with SPAZ-4 [(mouse×mouse) ×human] hybridoma. SPAZ-4 cells are known in the art and can be produced according to methods described in U.S. Pat. No. 4,634,664, which is hereby incorporated by reference. The SBIII×SPAZ-4 fused cells are grown in Dulbecco's modified minimal essential medium containing supplementary pyruvate, oxaloacetic acid, non-essential amino acids, 20% fetal calf serum (from a selected batch), hypoxanthine, aminopterin, and thymidine according to standard protocols. In addition, ouabain (10−$^7$H) is added to eradicate any unfused human B cells (which may secrete abundant HSV antibody and can be misleading in ELISA assays). The cells are cultured for two weeks with occasional medium changes, after which supernatants are tested for HSV antibody production with ELISA assays as described below.

C. Screen for antibody production

HSV antigen is prepared by infecting VERO cells with HSV-1 (McIntyre) at m.o.i=10. After culturing for 48 hrs.

cells are washed in PBS with centrifugation at 100 g for 10 min., and disrupted in 10 ml Vestergaard buffer per 180 cm² flask of cells. The detergent-disrupted lysates absorb to plastic wells and and are exposed to supernatants of the fused cells from Step B, supra. Antibody which binds to the HSV-1 is revealed with a peroxidase-conjugated goat antibody to human H and L chains (Tago, Burlingame, Calif.). The antigen-binding supernatants are identified and their respective cells are expanded in culture.

After 1–2 weeks in 2 ml wells, supernatants are re-tested for antigen binding and also for lack of binding to VERO host cell lysates. This test establishes preliminary evidence for specificity. The cells are then cloned four times at a seeding density of 30, 3, and 0.3 cells per 100 wells, and samples of live cells are stored frozen at each stage.

From one cell fusion, 30 cultures tested "positive" in the screening ELISA, an one of these, identified as 64-863 which had an intermediate score in the screening ELISA, is found to be stable for antibody production in continuous culture.

EXAMPLE 4

Optimization of 64-863 cultures

A high concentration of 64-863 cells ($10^7$ per ml) are cultured directly into serum-free media DMEM/F12 without any supplements. While most cells die, the surviving fraction grows well at high densities in serum free medium and produces high levels of antibody. Cells may be subcultured at approximately 14 day intervals by feeding with 50% volume additions on days 7 and 14.

In serum-free conditions, 64-863 cells proliferate and produce antibody in stationary cultures, but these cells will die in 3–5 days if placed in rotating bottles. If, however, the cells are cultured in 1% serum, rotation does not adversely affect cells.

Antibody may be harvested from "exhausted" supernatants by culturing cells at 37° C. and allowing the cultures to grow without further addition of medium. After 5–10 days the cell death is complete and the supernatant is clarified by centrifugation. Serologic tests using ELISA methods and a standard of pure 64-863 antibody show that cells grown in DMEM with 5% fetal calf serum (FCS) produce exhausted supernatants containing approximately 300 μg per ml monoclonal antibody and cells grown in DMEM with 0% FCS produce in excess of 60 μg per ml. This represents one of the highest ranges reported for monoclonal antibody production, regardless of origin.

The genetic stability of antibody production by 64-863 cells is demonstrated by testing antibody production of individual clones isolated from cells which are grown in protein-free media for over six months. 48 of 49 growing colonies produce 64-863 antibody.

EXAMPLE 5

Immunochemical Characterization

A. Antibody class/subclass: IgG1

The immunoglobulin class of antibody 64-863 is determined using ELISA methods. The antibody is captured on antigen-coated plates and the assay is developed with subclass specific, peroxidase-conjugated anti-human Ig (Tago). 64-863 is clearly identified as an IgG1 antibody.

B. Light Chain Type: λ

Using ELISA methods similar to those described in Step A, 64-863 is tested with anti κ or λ light chain reagents (Tago). The antibody is clearly identified as having λ light chains.

C. Binding to *Staphylococcus aureus* Protein A (SPA)

Antibodies are tested for the ability to bind to SpA by ELISA methods. Antibody 64-863 is captured on antigen, and the ELISA is developed with peroxidase-conjugated SpA. A strong stain identifies 64-863 as an SpA-binding immunoglobulin.

D. Polyacrylamide Gel Electrophoresis (PAGE)

To assess purity and homogeneity of 64-863 obtained from SpA purification, PAGE is performed. The antibody displays two bands of approximately 50–55 kD and 25–30 kD. Thus it is concluded that the antibody is homogeneous and highly pure after elution from SpA.

E. Isoelectric Focusing (IEF)

A sample of antibody 64-863 is applied to gel. 64-863 behaves as a highly basic protein.

F. Antigen Immunoprecipitation

To determine the molecular weight and state of glycosylation of the HSV antigen which is recognized by 64-863, immunoprecipitation of biosynthetically-labelled, mock-infected or infected with HSV-1 or HSV-2. In addition, the culture media are adjusted to supply $^{14}$C-glucosamine or $^{35}$S-methionine to the infected cells. The cells are dissolved in detergent buffer and the radiolabelled solutions are exposed to antibody 64-863 or to irrelevant antibody 53-2-4. The complexes of antigen plus antibody are captured on insoluble beads containing SpA and are dissolved, denatured and reduced in a sample buffer prior to PAGE analysis and radioautography. Antibody 64-863 precipitates an antigen of HSV-1 of 55 kD and an antigen of HSV-2 of 50–55 kD. The HSV antigen is glycosylated since $^{14}$C-glucosamine is incorporated into the molecule. Control, uninfected VERO cells, and antibody 53-2-4 do not display this prominent antigen. The molecules precipitated by 64-863 are identified as HSV-1 gD and HSV-2 gD using methods described in Eisenberg, et al., 1980 "Comparative structural analysis of glycoprotein gD of Herpes Simplex Virus types 1 and 2". *J. Virol.* Vol. 36: 428–435, which is hereby incorporated by reference.

G. Specificity of 64-863

To determine if 64-863 will recognize isolates of HSV-1 and HSV-2 which are present in the human population, antibody 64-863 is tested for its ability to react with HSV viruses of independent origin by ELISA assay. In addition, it is tested for reactivity with antigens of uninfected cells and antigens of cells infected with the distantly related virus varicella-zoster (VZ). Results show that 64-863 reacts with 15 independent isolates of HSV-1 and 15 independent isolates of HSV-2 but not at all with VERO or VZ antigens. Thus, the antigen recognized by 64-863 is shared by all herpes simplex virus isolates tested to date, but is not expressed by uninfected cells or cells infected by a different virus.

EXAMPLE 6

Biological Characterization

A. HSV neutralization by 64-863

Antibody 64-863 is purified and tested in a virus neutralization assay using HSV-1 and HSV-2. The microneutralization assay is designed so that 10 to 20 plaque forming units (p.f.u.) are present in each well in the presence of guinea pig complement (at 1:30) and antibody. After incubation for 30 min. at 37° C., the virus is transferred to susceptible VERO cells and incubated for 48 hours to allow plaques to become evident. Results show that high concentrations of 64-863 totally abolish the appearance of plaques. Doubling dilutions of antibody reveal of 50% inhibition of p.f.u. at an antibody concentration of 0.2 μg/mL, which defines the $IC_{50}$. Virtually identical results are obtained for HSV-1 and HSV-2 using 64-863.

B. Protection from HSV lethality in vivo

Mouse models of HSV-1 and HSV-2 disease are developed to assess the ability of 64-863 to protect young animals from HSV infection. Mice are chosen since only a small amount of antibody is required for thereapeutic dose levels and since it is possible to test large numbers of animals in dose-response analyses. Virulent forms of HSV-1 (strain Patton) and HSV-2 (333) are grown for use. Preliminary experiments established the appropriate doses for $LD_{50}$ in 3 week-old mice using HSV-1 for i.p. inoculation and HSV-2 for footpad inoculation. Protection by 64-863 is tested by dosing mice with $10\times LD_{50}$ and administering purified, 64-863 in phosphate buffered saline intraperitoneally.

Purifed antibody retains full specific functional activity: HSV-2 protection in vivo In one experiment, groups of 15 mice are administered either purified or unpurified 64-863 antibody 24 hours prior to inoculation with HSV-2 ($10\times LD_{50}$) in the footpad. Antibody is administered at 0, 1, 10, 100 or 1000 µg per animal. The percent survival after 21 days is given in Table I, below. As is evident from this table, the purified antibody activity is indistinguishable from that of the crude supernatant, and the purification procedure which involves a brief exposure to pH 3.5 has no detectable effect on antibody specific activity.

TABLE I

PROTECTION OF YOUNG MICE FROM LETHAL HSV-2 INFECTION BY HUMAN MONOCLONAL ANTIBODY 64.863

| PURIFIED ANTIBODY | | | CRUDE SUPERNATANT | | |
|---|---|---|---|---|---|
| Dose of Antibody (µg per animal) | N | % Survival | Dose of Antibody (µg per animal) | N | % Survival |
| 1000 | 15 | 100 | 1000 | 15 | 100 |
| 300 | 15 | 93.3 | 300 | 14 | 85.7 |
| 100 | 15 | 60.0 | 100 | 15 | 46.7 |
| 30 | 15 | 33.3 | 30 | 15 | 30.0 |
| 10 | 15 | 33.3 | 10 | 14 | 28.6 |
| 3.0 | 15 | 13.3 | 3.0 | 15 | 20.0 |
| 1.0 | 15 | 0 | 1.0 | 15 | 6.7 |
| 0.3 | 15 | 0 | 0.3 | 15 | 0 |
| PBS | 15 | 13.3 | | | |

Antibody 64.863 was administered i.p., 24 h prior to injection with $10\times LD_{50}$ of HSV-2 strain 333 in the footpad. Values are shown for survival at 21 days. This result demonstrates that immunoglobulin purification does not reduce the biological efficacy of antibody 64.863.

C. Protection from HSV-1

In a procedure similar to that described in Step B, above, groups of 13 young mice are treated with various doses of antibody 64-863 and challenged with HSV-1 intraperitoneally after 24 hours. Survival at 14 days is shown in Table II, below, $ED_{50}$ is 17 µg per animal. At high dosages antibody 64-863 provides complete protection.

TABLE II

PROTECTION OF YOUNG MICE FROM LETHAL HSV-1 INFECTION BY HUMAN MONOCLONAL ANTIBODY 64.863

| Dose of Antibody (µg per animal) | N | % Survival |
|---|---|---|
| 1000 | 14 | 100 |
| 300 | 13 | 92.3 |
| 100 | 13 | 76.9 |
| 30 | 13 | 69.2 |
| 10 | 13 | 23.1 |

TABLE II-continued

PROTECTION OF YOUNG MICE FROM LETHAL HSV-1 INFECTION BY HUMAN MONOCLONAL ANTIBODY 64.863

| Dose of Antibody (µg per animal) | N | % Survival |
|---|---|---|
| 1 | 12 | 8.3 |
| PBS | 11 | 0 |

C. Timing of 64-863 administration for protection in vivo

Two experiments are performed to analyze whether dosing with antibody is needed prior to virus challenge in order to be protective (prophylaxis), or if the antibody can be administered during or even after infection is established. As shown below in Tables III and IV, administration of 300 µg 64-863 antibody intraperitoneally prior to, or at the time of infection is highly effective to protect groups of 15 mice from infection with HSV-1 or HSV2. In the case of HSV-2 (which is spread slowly by predominantly neural routes) antibody is strongly protective even at 48 hours after infeciton. For HSV-1 (which spreads more rapidly through hematogenous routes), antibody is strongly protective to 24 hours after infection and showed weaker effects thereafter. Thus, 64-863 is protective whether administered prior to or subsequent to infection for both HSV-1 and HSV-2 infections.

TABLE III

TIMING OF ADMINISTRATION OF ANTIBODY 64.863 FOR PROTECTION OF YOUNG MICE FROM LETHAL HSV-1 INFECTION

| Dose of Antibody (µg per animal) | Day relative to virus challenge | N | % Survival |
|---|---|---|---|
| 300 µg 64.863 | −2 | 15 | 100 |
| " | −1 | 15 | 100 |
| " | 0 | 15 | 100 |
| " | +1 | 14 | 64.3 |
| " | +2 | 15 | 66.7 |
| " | +3 | 15 | 40.0 |
| " | +4 | 15 | 33.3 |
| " | +5 | 15 | 20.0 |
| " | +6 | 15 | 26.7 |
| " | +7 | 15 | 33.3 |
| " | +8 | 15 | 13.3 |
| " | +9 | 15 | 13.3 |
| " | +10 | 14 | 35.7 |
| " | +11 | 15 | 13.3 |
| PBS | −1 | 14 | 14.3 |
| 300 µg 53-2-4 | −1 | 15 | 40.0 |

Antibody 64.863 was administered at a dose of 300 µg per animal intraperitoneally at different time Intervals. $10 \times LD_{50}$ HSV-1 strain Patton was administered intraperitoneally at Day 0. Values are shown for survival at 21 days. 53-2-4 is a human $IgG_1$ NUB to tetanus toxin and serves as a negative control.

TABLE IV

TIMING OF ADMINISTRATION OF ANTIBODY 64.863 FOR PROTECTION OF YOUNG MICE FROM LETHAL HSV-2 INFECTION

| Dose of Antibody (µg per animal) | Day relative to virus challenge | N | % Survival |
|---|---|---|---|
| 300 µg 64.863 | −2 | 15 | 100 |
| " | −1 | 15 | 73.3 |
| " | 0 | 15 | 80.0 |
| " | +1 | 15 | 100.0 |

TABLE IV-continued

TIMING OF ADMINISTRATION OF ANTIBODY 64.863 FOR PROTECTION OF YOUNG MICE FROM LETHAL HSV-2 INFECTION

| Dose of Antibody (μg per animal) | Day relative to virus challenge | N | % Survival |
|---|---|---|---|
| " | +2 | 15 | 86.7 |
| " | +3 | 15 | 66.7 |
| " | +4 | 15 | 33.3 |
| " | +5 | 15 | 60.0 |
| " | +6 | 15 | 13.3 |
| " | +7 | 15 | 13.3 |
| " | +8 | 15 | 40.0 |
| " | +9 | 15 | 26.7 |
| " | +10 | 15 | 13.3 |
| " | +11 | 15 | 13.3 |
| PBS | 0 | 15 | 13.3 |
| 300 μg g 53-2-4 | 0 | 15 | 0 |

Antibody 64.863 was administered at a dose of 300 μg per animal intraperitoneally at different time intervals. $10 \times LD_{50}$ HSV-2 of strain 333 was administered in the footpad on day 0. Values are shown for survival at 21 days. 53-2-4 is a human $IgG_1$ MAB to tetanus toxin and serves as a negative control.

D. Potency of 64-863

To assess the relative potency of antibody 64-863, mice are treated with human immunoglobin (SANDOGLOBULIN®) or with 64-863. The specific activities of the two immunoglobulin preparations are compared in Tables V and VI below.

TABLE V

PROTECTION OF YOUNG MICE FROM LETHAL HSV-1 INFECTION BY SANDOGLOBULIN OR HUMAN MAB 64.863

| HUMAN MAB 64.863 | | | SANDOBLOBULIN | | |
|---|---|---|---|---|---|
| Dose of Antibody (μg per animal) | N | % Survival | Dose of Antibody (μg per animal) | N | % Survival |
| 300 | 14 | 85.7 | 100,000 | 15 | 100 |
| 100 | 15 | 86.7 | 30,000 | 15 | 100 |
| 30 | 15 | 53.3 | 10,000 | 15 | 100 |
| 10 | 15 | 46.7 | 3,000 | 15 | 86.7 |
| 3 | 15 | 26.7 | 1,000 | 14 | 78.6 |
| | | | 300 | 15 | 33.3 |
| | | | 100 | 15 | 33.3 |
| PBS | 15 | 0 | | | |

Antibody 64.863 and Sandoglobulin were administered i.p., 24 h prior to injection with $10 \times LD_{50}$ of HSV-1 strain Patton intraperitoneally. Values are shown for survival at 14 days.

TABLE VI

PROTECTION OF YOUNG MICE FROM LETHAL HSV-2 INFECTION BY SANDOGLOBULIN OR HUMAN MAB 64.863

| HUMAN MAB 64.863 | | | SANDOBLOBULIN | | |
|---|---|---|---|---|---|
| Dose of Antibody (μg per animal) | N | % Survival | Dose of Antibody (μg per animal) | N | % Survival |
| 300 | 15 | 93.3 | 100,000 | 15 | 73.3 |
| 100 | 15 | 73.3 | 30,000 | 15 | 66.7 |
| 30 | 15 | 53.3 | 10,000 | 15 | 40.0 |
| 10 | 15 | 26.6 | 3,000 | 15 | 26.7 |
| 3 | 14 | 7.1 | 1,000 | 15 | 26.7 |
| | | | 300 | 15 | 26.7 |
| | | | 100 | 15 | 0 |
| PBS | 15 | 20.0 | | | |

Antibody 64-863 and Sandeglobulin were administered i.p., 24 h prior to injection with $10 \times LD_{50}$ HSV-2 strain 333 in the footpad. Values are shown for survival at 21 days.

The results show that for HSV-1, human immunoglobin is protective at 300 μg per animal while 64-863 protects at a dose of 15 μg, (a potency factor of about 20 fold). For HSV-2, human immunoglobin is needed at about 15,000 μg per animal while 64-863 is effective at 25 μg (a potency factor of approximately 600). Thus 64-863 is much more potent than gamma globulin in the prophylaxis models of HSV infection for both HSV-1 and HSV-2. The large difference in dose of human immunoglobins effective for HSV-1 vs. HSV-2 prophylaxis may be explained by the known difference in titers of antibodies to those respective viruses which is seen in the population (many fewer people are seropositive for HSV-2 than for HSV-1).

E. 64-863 inhibits HSV lesion formation by virus discharge from neurons

A model of skin lesion formation, by HSV discharged from sensory neurons, is adapted to test the ability of 64-863 to inhibit the process of vital lesion recrudescence. Adult BALB/c mice are infected by scarification on the lateral thorax with HSV-1. After 5–7 days, severe band-like confluent lesions form unilaterally along the entire dermatome. This process is known to involve the centripetal ascent of virions to the dorsal root ganglia and centrifugal descent of virus within sensory afferents of the dermatome. Administration of 64-843 3 days after inoculation of virus substantially decreases the frequency and severity of lesion formation and prevents mortality as shown in Table VII, below. Thus antibody 64-863 can act at the time of discharge of virus from neurons to reduce the severity of lesion formation. Since the half-life of human antibody in the mouse is short, these results are unexpectedly favorable.

TABLE 7

HUMAN MAB 64-863 ACTION ON NEUROGENIC HSV ZOSTERIFORM DISEASE.

| | | Antiboy and Treatment (g per animal) | | | | |
|---|---|---|---|---|---|---|
| Lesion Score | PBS | 53-2-4 (1,000) | 64-863 (1,000) | 64-863 (300) | 64-863 (100) | 64-683 (30) |
| Death | 3 | 2 | | | 1 | 2 |
| 10 (severe band) | 9 | 6 | 3 | 4 | 5 | 5 |
| 6 (moderate band) | | 2 | 3 | 1 | 2 | 4 |
| 3 (few spots) | | 1 | 1 | | 2 | 1 |
| 1 | | | 4 | 6 | 1 | |
| 0 (nil) | | 1 | 1 | 2 | 1 | |
| Total animals | 12 | 12 | 12 | 14 | 13 | 12 |

Data are expressed as number of mice per category.

EXAMPLE 7

Preparation of 64-863 Fabs

Antibody 64-863 (0.5 to 1.5 mg/mL0 is dialyzed at 4° C. against 0.04M $Na_2HPO_4$, 0.01M $NaH_2PO_4$, 0.15M NaCl, 1 mM EDTA, and adjusted to pH 7.3 with HCl. One microliter of mercaptoethanol is added per mL of solution. Mercuripapain, 1/300 the mass of the IgG, is added and a stream of nitrogen is directed on top of the solution for a few seconds. The solution is sealed under Parafilm and incubated for 90 min at 37° C. The solution is then put on ice and one-tenth volume of 0.25M iodoacetamide is added. Incubation is for 0.5 hr on ince in the dark. The solution is then passed over a ouabain-Sepharose column (made according to Zurawski et al, J. Immunology (1978) 121 122). The column is washed with phosphate-buffered saline containing sodium azide, then 0.1M acetic acid, and finally 1M acetic acid. Radioimmunoassay usually reveals that most of the antibody activity is in the 0.1M acetic acid fraction. This fraction is neutralized with 1M sodium phosphate, pH 7.3, then dialyzed extensively against phosphate-buffered saline with no azide, and sterilized by filtration through 0.22 m filters.

An alternative method of digestion is to use one-tenth volume of 0.077M dithiothreitol (instead of mercaptoethanol) and 25 units of insoluble papin (papin attached to beaded agarose; one unit will hydrolyze 1.0 mole of N--benzoyl-L-arginineethyl ester (BAEE) per min at pH 7.0 at 30° C.) per 67 mg CH4-14 IgG. The solution is rocked constantly at 37° C. for 2 hrs. Iodoacetamide is added as previously described except the concentration of the stock solution is only 0.16M. This method can also be used with concentrated cell supernatant that has been dialyzed against the phosphate buffer mentioned above if the protein from the fetal calf serum is approximatley the same or lower in concentration than the 64-863 cell.

An alternative method of isolating Fab fragments from the digestion mixture is to dialyze the digested antibody against phosphate-buffered saline and remove the Fc fragments by passage through a Protein A column equilibrated in phospate-buffered saline. This procedure can also be used to remove any undigested IgG after chromatography on the ouabain-Sepharose column.

EXAMPLE 8

Nucleotide and Amino Acid Sequence of 64-863 Variable Domains

The genes encoding the heavy and light chains of antibodies secreted by trioma cell lines are cloned according to methods described in Sambrook et al., *Molecular Cloning: A Laboratory Manual*, (2nd ed., Cold Spring Harbor, N.Y., 1989; Berger & Kimmel, *Methods in Enzymology, Volume 152, Guide to Molecular Cloning Techniques*, (Academic Press, San Diego, Calif., 1987); Co et al., *J. Immunol.*, 148:1149 (1992) (each of which is incorporated by reference in its entirety for all purposes). For example, genes encoding heavy and light chains are cloned from a trioma's cDNA produced by reverse transcription of the trioma's mRNA. Cloning is accomplished by conventional techniques including the use of PCR primers that hybridize to an enzymatically inserted sequence (e.g., a G tail) or to the sequences flanking or overlapping the genes, or segments of genes, to be cloned. The cDNA and predicted amino acid sequences of the heavy and light chain variable domains from the 64-863 antibody are shown in FIG. 1.

The provision of amino acid sequences for the 64-863 antibody can be exploited to provide alternate means for generating antibodies having the same or similar binding specificity. That is, antibodies that bind to the same epitope as the 64-863 antibody or an epitope sufficiently proximal to that bound by the 64-863 antibody to compete with the 64-863 antibody for binding to the-HSV I and/or -II glycoprotein. Such antibodies can, of course, also be produced using the same procedure as noted for the 64-863 antibody, employing the 64-863 antibody as a reference for selection of appropriate binding specificity. However, generation of variants from sequence data has the advantage of avoiding the need for immunization and immortalization.

Many of the amino acids in the disclosed 64-863 sequences can undergo non-critical substitutions, additions or deletions without loss of binding specificity or effector functions, or intolerable reduction of binding affinity (i.e., below about $10^7$ $M^{-1}$). Thus, the binding affinity of most antibodies is within a range of about $10^7$ $M^{-1}$ or $10^8$ $M^{-1}$ to about $10^9$ $M^{-1}$. Usually, antibody chains incorporating such alterations exhibit substantial sequence identity to the reference antibody chain from which they were derived. For example, the mature light chain of antibodies derived from the 64-863 antibody usually shows substantial sequence identity (i.e., at least 75, 85% or 95%) to the sequence of the mature light chain of the 64-863 antibody shown in FIG. 1 (panel A). Similarly, the mature heavy chains of derivatives typically show substantial sequence identity to the sequence of the mature heavy chain of the 64-863 antibody shown in FIG. 1 (panel B). Sequence identity comparisons are performed between two polypeptide sequences when optimally aligned, such as by the programs BLAZE (Intelligenetics) GAP or BESTFIT using default gap weights. Usually, antibodies comprise two identical pairs of heavy and light chains. However, bifunctional antibodies can be produced that have one heavy/light chain pair specific for the gD antigen and the other heavy/light chain pair specific for a second antigen.

Conservative substitutions (as defined by, e.g., Co, WO 94/12215 (incorporated by reference in its entirety for all purposes)) at positions other than the CDR regions and amino acids interacting closely with the CDR regions (see Queen et al., WO 90/07861 (incorporated by reference in its entirety for all purposes) are likely to have little effect on the functional properties of antibodies, such as binding affinity, kinetics and specificity. However, in general, derivatives harboring such mutations are not preferred in comparison with the original 64-863 antibody. Mutations within the CDR regions and at positions closely interacting with these regions, particularly nonconservative mutations, generally result in greater changes in the functional properties of an antibody. Occasionally, a mutated antibody is selected having the same specificity and increased affinity or faster binding kinetics compared with the 64-863 antibody. Usually, the affinity of the mutated antibody is within a factor of 2, 5, 10 or 50 of the 64-863 antibody. Phage-display technology offers powerful techniques for selecting such antibodies. See, e.g., Dower et al., WO 91/17271; McCafferty et al., WO 92/01047; Huse, WO 92/06204 (each of which is incorporated by reference in its entirety for all purposes).

The variable segments of human antibodies produced as described supra are typically linked to at least a portion of an antibody constant region (Fc), typically that of a human antibody. Human constant region DNA sequences can be isolated in accordance with well-known procedures from a variety of human cells, but preferably immortalized B-cells (see Kabat et al., *Sequences of Proteins of Immunological Interest* (National Institutes of Health, Bethesda, Md. (1987) and (1991)), and WO87/02671) (each of which is incorporated by reference in its entirety for all purposes). Ordinarily, the antibody will contain both light chain and heavy chain constant regions. The heavy chain constant region usually includes CH1, hinge, CH2, CH3, and sometimes CH4 regions. The present antibodies include antibodies having all types of constant regions, including IgM, IgG, IgD, IgA and IgE, and any isotype, including IgG1, IgG2, IgG3 and IgG4. When it is desired that the human antibody exhibit cytotoxic activity, the constant domain is usually a complement-fixing constant domain and the class is typically IgG1, IgG3, IgM. When such cytotoxic activity is not desirable, the constant domain may be of the IgG2 or IgG4 class. The human antibody can comprise sequences from more than one class or isotype.

Also provided in isolated form are DNA segments encoding heavy or light chains of the antibodies described supra. The DNA segments encode at least one CDR regions and usually all three CDR regions from the heavy or light chain of an antibody. Frequently, a DNA segment encodes all or substantially all of the variable region of a heavy or light chain and is thereby capable of exhibiting antigen binding capacity. Often a nucleic acid encodes an entire heavy or light chain. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Preferred nucleic acids include those encoding mature light chain variable regions having substantial sequence identity to the mature light chain variable region of the 64-863 antibody shown in FIG. 1 (Panel A) (SEQ. ID. No. 4). Preferred nucleic acids also include those encoding mature heavy chain variable regions having substantial sequence identity to the mature heavy chain variable region of the 64-863 antibody shown in FIG. 1 (panel B) (SEQ. ID. No. 2).

What is claimed is:

1. A human monoclonal antibody that binds to a gD antigen of Herpes Simplex Virus-1 (HSV-1) and Herpes Simplex Virus-2 (HSV-2) and neutralizes said viruses, said monoclonal antibody designated 64-683.

2. A human monoclonal antibody that neutralizes HSV-I and HSV-II, said monoclonal antibody designated SB-IV-6-2 (ATCC HB 9316).

3. A cell line producing the antibody of claim 1.

4. A cell line producing the antibody of claim 2.

5. The cell line of claim 4, designated ATCC HB9316.

6. The cell line of claim 3 that is a trioma cell line.

7. The cell line of claim 6, designated ATCC.

8. A fragment of the antibody of claim 1, wherein said fragment binds to the glycoprotein gD antigert of HSV-1 and HSV-2.

9. The fragment of claim 8 wherein said fragment is a Fab fragment.

10. A fragment of the antibody of claim 2, wherein said fragment binds to the glycoprotein gD antigen of HSV-I and HSV-2.

11. The fragment of claim 10 wherein said fragment is a Fab fragment.

12. An antibody comprising a mature light chain variable region having at least 85% sequence identity to the mature light chain variable sequence of SEQ. ID. No. 4 and a mature heavy chain variable region having at least 85% sequence identity to the mature heavty chain variable sequence of SEQ. ID. No. 2, wherein the antibody neutralizes HSV-I and HSV-II in vivo, and competes with the monoclonal antibody designated 64-863 for binding to the gD antigen of HSV-I and -II.

13. The antibody of claim 12, wherein the mature light chain variable region comprises the three CDR regions of the sequence of SEQ. ID. No. 4, and the heavy chain variable region comprises the three CDR regions of the sequence of SEQ. ID. No. 2.

14. The cell line of claim 3, containing the mature coding region of SEQ. ID. Nos. 1 and 3, which are expressed to produce the heavy and light chains of the monoclonal antibody.

* * * * *

UNITED STATES PATENT AND TRADEMARK OFFICE
CERTIFICATE OF CORRECTION

PATENT NO. : 5,646,041
DATED : July 8, 1997
INVENTOR(S) : Harfeldt et al

It is certified that error appears in the above-identified patent and that said Letters Patent is hereby corrected as shown below:

In the claims:

1. A human monoclonal antibody that binds to a gD antigen of Herpes Simplex Virus-1 (HSV-1) and Herpes Simplex Virus-2 (HSV-2) and neutralizes said viruses, said monoclonal antibody designated [64-683] 64-863 (ATCC HB 9316).

7. The cell line of claim 6, designated ATCC HB 12304.

8. A fragment of the antibody of claim 1, wherein said fragment binds to the glycoprotein gD [antigert] antigen of HSV-1 and HSV-2.

UNITED STATES PATENT AND TRADEMARK OFFICE
CERTIFICATE OF CORRECTION

PATENT NO. : 5,646,041
DATED : July 8, 1997
INVENTOR(S) : Harfeldt, et al.

It is certified that error appears in the above-identified patent and that said Letters Patent is hereby corrected as shown below:

12. An antibody comprising a mature light chain variable region having at least 85% sequence identity to the mature light chain variable sequence of SEQ. ID. No. 4 and a mature heavy chain variable region having at least 85% sequence identity to the mature [heavty] heavy chain variable sequence of SEQ. ID. No. 2, wherein the antibody neutralizes HSV-I and HSV-II in vivo, and competes with the monoclonal antibody designated 64-863 --ATTC HB 12304--for binding to the gD antigen of HSV-I and-II.

Signed and Sealed this

Twenty-fourth Day of February, 1998

Attest:

BRUCE LEHMAN

*Attesting Officer*    Commissioner of Patents and Trademarks